(12) United States Patent
Haycock

(10) Patent No.: US 7,037,670 B2
(45) Date of Patent: May 2, 2006

(54) PEPTIDE SUBSTRATES FOR ASSAY OF EXTRACELLULAR SIGNAL-REGULATED PROTEIN KINASE 1 AND 2 ACTIVITY

(75) Inventor: John W. Haycock, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 755 days.

(21) Appl. No.: 10/126,834

(22) Filed: Apr. 19, 2002

(65) Prior Publication Data

US 2005/0054023 A1 Mar. 10, 2005

(51) Int. Cl.
*C12G 1/48* (2006.01)
*C12N 9/10* (2006.01)
*C12N 1/00* (2006.01)
*C07K 5/00* (2006.01)

(52) U.S. Cl. .................. 435/15; 435/193; 435/810; 530/326; 530/327

(58) Field of Classification Search .............. 435/15, 435/193, 810; 530/326, 327
See application file for complete search history.

(56) References Cited

U.S. PATENT DOCUMENTS

| | | | |
|---|---|---|---|
| 5,532,167 A | 7/1996 | Cantley et al. | 436/89 |
| 6,348,310 B1 | 2/2002 | Goueli | 435/4 |

OTHER PUBLICATIONS

Clark–Lewis, I. et al., "Definition of a consensus sequence for peptide substrate recognition by p44$^{mph}$, the meiosis–activated myelin basic protein kinase," J. Biol. Chem., vol. 266, pp. 15180–15184 (1991).

Erickson, A.K. et al., "Identification by mass spectrometry of threonine 97 in myelin basic protein as a specific phosphorylation site for mitogen–activated protein kinase," J. Biol. Chem., vol. 265, pp. 19728–19735 (1990).

Gonzalez, F.A. et al., "Identification of substrate recognition determinants for human ERK1 and ERK2 protein kinases," J. Biol. Chem., vol. 266, pp. 22159–22163 (1991).

Haycock, J.W., "In vivo activation of ERK1 and ERK2 in regions of rat brain," Neural Notes, vol. 2, pp. 14 (1996).

Haycock, J.W. et al., "ERK1 and ERK2, two microtubule–associated protein 2 kinases, mediate the phosphorylation of tyrosine hydroxylase at serine 31 in situ," Proc. Natl. Acad. Sci. USA, vol. 89, pp. 2365–2369 (1992).

Haycock, J.W., "Peptide substrates for ERK1/2: structure-function studies of serine 31 in tyrosine hydroxylase," Journal of Neuroscience Methods, to be published.

Kameshita, I. et al., "A new peptide conjugate as a highly specific substrate for MAP kinase," J. Biochem., vol. 122, pp. 168–172 (1997).

Kulich, S.M. et al., "Sustained extracellular signal–regulated kinase activation by 6–hydroxydopamine: implications for Parkinson's disease," J. Neurochem., vol. 77, pp. 1058–1066 (2001).

Ortiz et al., "Extracellular signal–regulated protein kinases (ERKs) and ERK kinase (MEK) in brain: Regional distribution and regulation by chronic morphine," J Neurosci., vol. 15, pp. 1285–1297 (1995).

Pearson, G. et al., "Mitogen–Activated Protein (MAP) Kinase Pathways: Regulation and phsyiological function," Endocrine Reviews, vol. 22, pp. 153–183 (2001).

Robinson, M.J. et al., "Mutation of position 52 in ERK2 creates a nonproductive binding mode for adenosine 5'–triphosphate," Biochem., vol. 355, pp. 5641–5646 (1996).

*Primary Examiner*—Jean C. Witz
*Assistant Examiner*—Susan Hanley
(74) *Attorney, Agent, or Firm*—Bonnie J. Davis; John H. Runnels

(57) ABSTRACT

Several synthetic peptides modeled after Ser31 in tyrosine hydroxylase ("Ser31 peptides") have been developed and evaluated as in vitro substrates for assaying the activity of extracellular signal-regulated protein kinase 1 and 2 ("ERK1/2"). The phosphorylation of the Ser31 peptides by activated, recombinant ERK2 was found to exhibit catalytic efficiencies ($V_{max}/K_m$) up to 4-fold higher than that of a synthetic myelin basic protein (MBP)-based peptide. Several synthetic peptides were tested using cellular extracts from PC12 rat pheochromocytoma cells, both untreated cells and cells treated with nerve growth factor. Although the phosphorylation of the MBP peptide by extracts of PC12 cells was higher than that of the Ser31 peptide, the relative treatment-dependent increase was much greater for the Ser31 peptide and the pattern of ERK1/2 activation more closely mimicked the pattern seen with more complicated assays that initially isolated ERK1/2 from other kinases in the cellular extracts. This result suggested that the Ser31 peptide was a more specific substrate for the ERK1/2. Use of the new Ser31 peptide substrates will decrease the amount of peptide required to assay for ERK1/2 activity. In addition, the higher catalytic efficiencies associated with greater specificity for ERK1/2 will enable researchers to assay for activity of ERK1/2 in cellular extracts without prior immunoprecipitation.

26 Claims, 6 Drawing Sheets

PEPTIDE SUBSTRATES FOR ASSAY OF EXTRACELLULAR SIGNAL-REGULATED PROTEIN KINASE 1 AND 2 ACTIVITY

The development of this invention was partially funded by the Government under U.S. Public Health Service grants MH00967, MH55208, and NS25134. The Government has certain rights in this invention.

This invention pertains to an assay for activity of extracellular signal-regulated protein kinases 1 and 2 ("ERK1" and "ERK2"), and to peptide substrates designed to optimize the catalytic efficiency and enzyme specificity for ERK1 and ERK2 activity.

The activity of cells is often regulated by extracellular inhibitory or stimulatory signals that are transmitted into the cell to elicit an intracellular response. This process of signal transmission culminating in an intracellular response is called "signal transduction." Protein kinases are enzymes involved in signal transduction. Protein kinases function by catalyzing the transfer of a phosphoryl group usually from adenosine triphosphate (ATP) to another protein in a process called "protein phosphorylation." The protein substrate targeted by the kinase may be a structural protein or another enzyme. Protein kinases have been shown to be key regulators of many cell functions, including signal transduction, transcription, cell motility, and cell division. Protein kinases are divided into two family groups based on the amino acid residue of the protein substrate that is phosphorylated. The first family consists of serine/threonine kinases, which are usually found in the cytoplasm or associated with particular intracellular region. The second family consists of tyrosine kinases, which are present in smaller quantities and include several membrane receptors for growth factors and hormones. See U.S. Pat. Nos. 5,532,167; and 6,348,310.

One of the primary signaling networks in signal transduction involves a protein kinase cascade, using kinases known collectively as "mitogen-activated protein (MAP) kinases." In this cascade, the initial protein kinase is activated and then in turn phosphorylates, and thus activates, the next tier of protein kinases in the cascade. This activation pattern is repeated until the final MAP kinase is activated. The MAP kinase cascade comprises at least three protein kinases in series that culminate in the activation of multifunction MAP kinases. In the currently known MAP kinase cascades, the kinase immediately upstream of the final MAP kinase is a member of the extracellular signal-regulated kinase ("ERK") kinase family. Signaling networks involving MAP kinase cascades are involved in controlling embryogenesis, cell differentiation, cell proliferation, and cell death.

Extracellular signal-regulated protein kinases 1 and 2 ("ERK 1/2") are the two most studied members of the family of serine/threonine protein kinases which are part of the MAP kinase cascade. See J. W. Haycock, "In vivo activation of ERK1 and ERK2 in regions of rat brain," Neural Notes, vol. 2, pp. 14 (1996). ERK1 and ERK2 are proteins of similar size (43 and 41 kDa respectively) with a nearly identical sequence (85% overall identity). ERKs are activated by conjoint phosphorylation of both a threonine and a tyrosine residue, which are located near the active site of the enzyme. Both ERK1 and ERK2 are ubiquitously expressed, but are most abundant in brain and spinal cord. The relative distribution of the two forms may vary with tissue. For example, ERK2 is the predominant form in immune cells, while in neuroendocrine cells the two forms are more equally expressed.

ERK1 and ERK2 have been shown to be activated in response to a great number of factors, including growth factors (e.g., epidermal growth factor and nerve growth factor), cytokines, and stress. See G. Pearson et al., "Mitogen-Activated Protein (MAP) Kinase Pathways: Regulation and physiological function," Endocrine Reviews, vol. 22, pp. 153–183 (2001). Nerve growth factor (NGF) is a potent activator of ERK1/2 in neuronal cells, where ERK1/2 mediate the phosphorylation of serine-31 in tyrosine hydroxylase, the rate-limiting enzyme in catecholamine synthesis. See J. W. Haycock et al., "ERK1 and ERK2, two microtubule-associated protein 2 kinases, mediate the phosphorylation of tyrosine hydroxylase at serine 31 in situ," Proc. Natl. Acad. Sci. USA, vol. 89, pp. 2365–2369 (1992); and Haycock, 1996. ERK1/2 activation is also a major step in many abnormal cell functions, including apoptosis, neuronal cytotoxicity, and oxidative neuronal injury. Abnormal activation of ERK1/2 has been implicated in both Alzheimer's and Parkinson's diseases. See S. M. Kulich et al., "Sustained extracellular signal-regulated kinase activation by 6-hydroxydopamine: implications for Parkinson's disease," J. Neurochem., vol. 77, pp. 1058–1066 (2001).

There are currently several approaches which are used to assay activity of ERKs, and thus the state of ERK activation within cells. These include in vitro phosphorylation of exogenous substrate by cellular extracts, in vitro phosphorylation of an exogenous substrate by ERK immunoprecipitates, in-gel phosphorylation of exogenous substrate, and quantitative blot immunolabeling of the diphosphorylated forms of ERK1/2. The first, and easiest, assay using cellular extracts without further purification requires that the substrate be selectively phosphorylated by ERK1/2. Whereas myelin basic protein ("MBP") exhibits better in vitro characteristics of phosphorylation by ERK than any other known substrate, an assay using MBP is not specific for ERK1/2 activity because MBP can be phosphorylated by a number of other cellular protein kinases. Whereas immunoprecipitation prior to kinase assay eliminates contributions from extraneous protein kinases, this assay requires additional steps and costly reagents. Similarly blot immunolabeling analyses are more complicated and costly than a simple assay, and require careful attention to ERK transfer efficiencies, which can be low and vary with sample composition. See J. Ortiz et al., "Extracellular signal-regulated protein kinases (ERKs) and ERK kinase (MEK) in brain: Regional distribution and regulation by chronic morphine," J. Neurosci., vol. 15, pp.1285–1297 (1995).

A simple assay that is specific for ERK1/2 activity and that relies on phosphorylation of a protein or peptide substrate requires efficient and specific substrates available in adequate quantity. Synthetic peptide substrates have been successfully used for some MAP protein kinases in crude extracts. However, the peptides used thus far are known to serve as substrates for several protein kinases, e.g., MBP and MBP peptide. See I. Kameshita et a., "A new peptide conjugate as a highly specific substrate for MAP kinase," J. Biochem., vol. 122, pp. 168–172 (1997). Based upon analysis of structure and function, a synthetic peptide substrate was developed for the ERKs modeled after the Thr97 phosphorylation site in MBP. See A. K. Erickson et al., "Identification by mass spectrometry of threonine 97 in myelin basic protein as a specific phosphorylation site for mitogen-activated protein kinase," J. Biol. Chem., vol. 265, pp. 19728–19735 (1990). This peptide, also called "MBP-tide" (APRTPGGRR, SEQ ID NO: 2), contains the—P-X-S/T-P—motif thought to represent the consensus substrate recognition sequence for both ERK1 and ERK2. See I.

Clark-Lewis et al., "Definition of a consensus sequence for peptide substrate recognition by p44$^{mpk}$, the meiosis-activated myelin basic protein kinase," J. Biol. Chem., vol. 266, pp. 15180–15184 (1991); and F. A. Gonzalez et al., "Identification of substrate recognition determinants for human ERK1 and ERK2 protein kinases," J. Biol. Chem., vol. 266, pp. 22159–22163 (1991). MBP has been shown to be phosphorylated by ERK2 at another site Thr94 and by numerous other protein kinases at other sites. See Erickson et al. 1990; and M. J. Robinson et al., "Mutation of position 52 in ERK2 creates a nonproductive binding mode for adenosine 5'-triphosphate," Biochem., vol. 355, pp. 5641–5646 (1996).

An alternative peptide substrate for ERK1 and ERK2, "ERKtide" (ATGPLSPGPFGRR, SEQ ID NO: 23), was developed. Although relatively efficient as a substrate for catalysis-poor ERK mutants, its kinetic characteristics were only quantitatively superior to previously described peptide substrates. See Robinson et al., 1996. The first Ser31-based peptide used as an ERK substrate was a rat tyrosine hydroxylase ("TH")-Ser31 peptide (KQAEAVTSPR, SEQ ID NO: 7). (Haycock et al., 1992). Although phosphorylated by both ERK1 and ERK2, this peptide incorporated considerably less $^{32}$P than did myelin basic protein ("MBP"). While the presence of a prolyl residue at the −2 position enhances the $V_{max}$ of peptide phosphorylation, its presence is not essential. See Clark-Lewis et al., 1991. In fact, the phosphorylation site of the first physiological substrate of ERK1/ERK2 to be described—Ser31 in tyrosine hydroxylase—does not possess such an upstream prolyl residue (rodent:—EAVTS$^{31}$PRFIGRR (SEQ ID NO: 9)—; other mammals:—EAIMS$^{31}$PRFK (SEQ ID NO: 10)—. See J. W. Haycock et al., "ERK1 and ERK2, two microtubule-associated protein 2 kinases, mediate the phosphorylation of tyrosine hydroxylase at serine 31 in situ," Proc. Natl. Acad. Sci. USA, vol. 89, pp. 2365–2369 (1992). There exists a need for peptide substrates with greater specificity for ERK1/2 to use in a simple assay for ERK1/2 activity.

I have developed synthetic peptides modeled around Ser31 in human tyrosine hydroxylase ("Ser31 peptides"), and evaluated these peptides as in vitro substrates for assaying the activity of extracellular signal-regulated protein kinase 1 and 2 ("ERK1/2"). The phosphorylation of the Ser31 peptides by activated, recombinant ERK2 was found to exhibit catalytic efficiencies ($V_{max}/K_m$) up to 4-fold higher than that of a synthetic myelin basic protein (MBP)-based peptide. Several synthetic peptides were tested using cellular extracts from PC12 rat pheochromocytoma cells, both untreated cells and cells treated with nerve growth factor. Although the phosphorylation of the MBP peptide by extracts of PC12 cells was higher than that of the Ser31 peptide, the relative treatment-dependent increase was much greater for the Ser31 peptide and the pattern of ERK1/2 activation more closely mimicked the pattern seen with more complicated assays that initially isolated ERK1/2 from other kinases in the cellular extract. This result suggested that the Ser31 peptide was a more specific substrate for the ERK1/2. Use of the new Ser31 peptide substrates will decrease the amount of peptide required to assay for ERK1/2 activity. In addition, the higher catalytic efficiencies associated with greater specificity for ERK1/2 will enable researchers to assay for activity of ERK1/2 in cellular extracts without prior immunoprecipitation.

EXAMPLE 1

Materials and Methods

Figure 1:
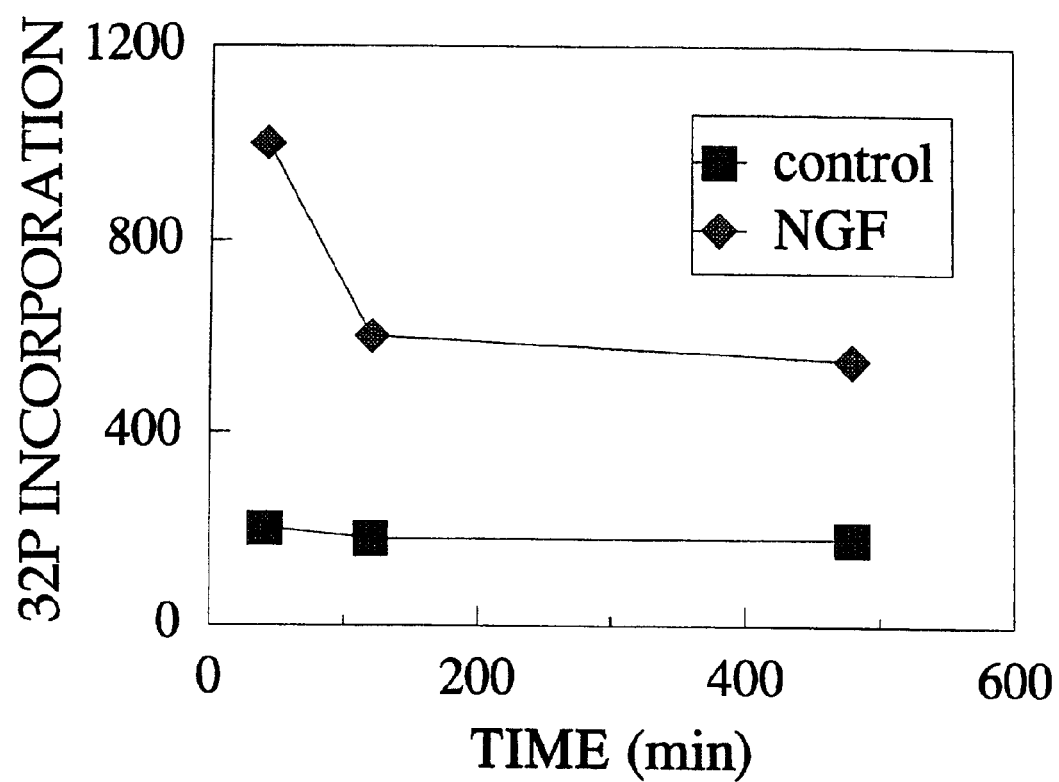
FIG. 1 illustrates the pattern of ERK1/2 activation in PC12 cells treated with and without nerve growth factor using an in vitro kinase assay on cellular extracts after other kinases in the extract were removed by immunoprecipitation, and using as substrate myelin basic protein (MBP; SEQ ID NO: 1).

Materials: Purified peptides were obtained from Sigma (St. Louis, Mo.) or custom synthesized by Louisiana State University Health Science Center Core Laboratories (New Orleans La.). Purified, activated ERK1 was a gift from Dr. M. H. Cobb (University of Texas Southwestern Medical Center, Dallas, Tex.). Purified, recombinant, activated ERK2 was a gift from Dr. N. G. Ahn (University of Colorado, Boulder, Colo.). Except as indicated below, other materials were purchased from Sigma. Table 1 is a list of the peptides used for the following assays. The new synthetic peptides modeled after Ser31 in human tyrosine hydroxylase are indicated.

TABLE 1

Peptide Substrates for ERK1/2

| SUBSTRATE SOURCE | SEQUENCE | SEQ ID NO: |
|---|---|---|
| MBP (protein) | . . . KNIVTPRTPPPS . . . | 1 |
| MBPtide (Thr97) | APRTPGGRR | 2 |
| EGF RECEPTOR (Thr669) | RRELVEPLTPSGEA | 3 |
| Th (rat) | | |
| Ser8 | PTPSAPSPQPK | 4 |
| Ser19 | RRAVSEQDAK | 5 |
| Ser40 | GRRQSLIEDAR | 6 |
| TH-Ser31 (rat): | KQAEAVTSPR | 7 |
| | AVTSPRFIGRR | 8 |
| | EAVTSPRFIGRR | 9 |
| TH-31: type 1 HUMAN: | EAIMSPRFK | 10 |
| | AIMSPRFIGRR | 11 |
| | EAIMSPRFIGRR | 12 |
| New | YQAEAIMSPRFIGRRQ | 13 |

TABLE 1-continued

Peptide Substrates for ERK1/2

| SUBSTRATE SOURCE | SEQUENCE | SEQ ID NO: |
|---|---|---|
| New | YQAEAIMSPRFIGRR-NH2 | 14 |
| New | QAEAIMSPRFGRR-NH2 | 15 |
| New | YQATGPLSPGPFRR-NH2 | 16 |
| New | QATGPLSPGPFRR-NH2 | 17 |
| New | YQATGPLSPGERR-NH2 | 18 |
| New | QATGPLSPGFRR-NH2 | 19 |
| Th-Ser31: type 2 HUMAN | IMVRGQSPR | 20 |
| | YIMVRGQSPR | 21 |
| | EAIMVRGQSPRFK | 22 |
| ERKtide: | ATGPLSPFGRR | 23 |

PC12 cells: PC12 rat pheochromocytoma cells (ATCC no. CRL-1721, American Type Culture Collection, Manassas, Va.) were maintained in culture and seeded into collagen-coated 12-well plates prior to the experiments, as described in J. W. Haycock et al., "ERK1 and ERK2, two microtubule-associated protein 2 kinases, mediate the phosphorylation of tyrosine hydroxylase at serine 31 in situ," Proc. Natl. Acad. Sci. USA, vol. 89, pp. 2365–2369 (1992). Cells were treated with or without added 100 ng/ml 7S nerve growth factor for up to 8 h. One group of cells was harvested for blot immunolabeling and solubilized with sodium dodecyl sulfate solution, as described in J. W. Haycock, "Multiple forms of tyrosine hydroxylase in human neuroblastoma cells: Quantitation with isoform-specific antibodies," J. Neurochem., vol. 60, pp. 493–502 (1993a). A second group of cells was harvested for kinase assays and subjected to trituration in an ice-cold lysis solution of 50 mM β-glycerophosphate, 1 mM EGTA, 1 mM dithiothreitol, 1 mM benzamidine (Eastman Kodak Co., Rochester, N.Y.), 0.1 mM $Na_3VO_4$, 10 µg/ml leupeptin, and 0.05% Tween 20. Supernatants from the latter samples were generated by sonication and centrifugation (20 min at 10,000×g) in a refrigerated centrifuge (Savant, Farmingdale, N.J.). In some experiments, ERK1/2 was isolated prior to assaying kinase activity by immunoprecipitation of the PC12 cellular extracts with anti-pan ERK1/2 and protein A-Sepharose. See Ortiz et al., 1995.

ERK activity assays: Aliquots of supernatants or ERK1/2 immunoprecipitates (suspended in lysis solution) were mixed with substrate (1 mM final, unless stated otherwise) at 4° C. Phosphorylation reactions were initiated by addition of an equal volume of assay buffer containing [$\gamma$-$^{32}$P]ATP (NEN Life Sciences Products, now PerkinElmer Life Sciences, Boston, Mass.) and $Mg^{++}$ and allowed to proceed for 10 min at 30° C., after which duplicate 20 µl aliquots were spotted onto Whatman P81 paper. As would be predicted by the presence of multiple basic residues in the peptides, the ability of P81 paper to bind >90% of each of the peptides used in Tables 2 and 3 was confirmed by UV detection following RP-HPLC. The final reaction mixtures (50 µl) contained 50 mM β-glycerophosphate, 10 mM $MgCl_2$, 1 mM EGTA, 1 mM dithiothreitol, 1 mM benzamidine, 0.1 mM ATP, 0.1 mM $Na_3VO_4$, 10 µM calmidazolium, 2 µM peptide inhibitor of cyclic AMP-dependent protein kinase (TTYADFIASGRTGRRNALHD, SEQ ID NO: 24), 10 µg/ml leupeptin, and 0.025% Tween 20.

Blot immunolabeling: The levels of diphosphorylated ERK protein were quantitated as described in detail in Ortiz et al., 1995; and Haycock, 1996. Aliquots were subjected to SDS-PAGE (9% slab gels), and proteins in the separating gel were transferred electrophoretically to nitrocellulose sheets. After protein staining (Ponceau S) was documented xerographically, transfers were then destained and quenched in blot buffer (Dulbecco's phosphate-buffered saline (GIBCO Invitrogen Corp., Carlsbad, Calif.), 10 mM Tris-HCl (pH 7.6), 0.05% (w/v) Tween20, and 0.01% sodium azide) containing 1% (w/v) polyvinylpyrrolidone as described in J. W. Haycock, "Polyvinylpyrrolidone as a blocking agent in immunochemical studies," Anal. Biochem. vol. 208, pp. 397–399 (1993b). Transfers were then incubated (1 hr, room temperature) sequentially with primary antibody (Promega, Madison, Wis.), swine anti-rabbit secondary antibody (0.8 µg/ml; DAKO, Glostrup, Denmark), and $^{125}$I-protein A (200 kcpm/ml; NEN Life Sciences Products) in blot buffer containing polyvinylpyrrolidone. Transfers were rinsed 5 times (2×2 min, 3×5 min) with blot buffer after incubation with each of the reagents. Immunoreactivity was visualized autoradiographically (XAR film; Eastman Kodak Co.), quantitated by gamma counting of excised bands and blanks, and expressed as relative protein levels by interpolation from standard curves run on the same blot (see Haycock, 1993a).

EXAMPLE 2

Phosphorylation of Peptide Substrates by ERKs

To test the effectiveness of various peptide substrates, peptide substrates were compared with myelin basic protein ("MBP," SEQ ED NO: 1) for relative ability to be phosphorylated by purified ERK1 or ERK2. The ERK activity assay was as described above in Example 1. The results using ERK1 are shown in Table 2. In Table 2, each value represents the median of three independent determinations, performed in duplicate. While all peptides were assayed at a concentration of 1 mM, MBP phosphorylation—given as a frame of reference at a concentration typically used in such assays—was assayed at 20 µM. $^{32}$P incorporation into MBPtide (SEQ ID NO: 2) was 330 nmol/min/mg under the assay conditions used.

As shown in Table 2, ERK1-dependent phosphorylation of MBP (SEQ ID NO: 1), MBP peptide (SEQ ID NO: 2), and epidermal growth factor ("EGF") receptor peptide (SEQ ID NO: 3) was substantially higher than that of rat TH-Ser31 peptide (SEQ ID NO: 7). $^{32}$P incorporation into this peptide was, however, higher than other rat TH peptides containing either Ser8 (SEQ ID NO: 4), Ser19 (SEQ ID NO: 5), or Ser40 (SEQ ID NO: 6).

TABLE 2

Phosphorylation of substrates by ERK1

| SUBSTRATE SOURCE | SEQUENCE | RELATIVE $^{32}$P INCORPORATION (% OF MBP) |
|---|---|---|
| MBP (protein) (SEQ ID NO: 1) | ... KNIVTPRTPPPS ... | 100 |
| MBPtide (Thr97) (SEQ ID NO: 2) | APRTPGGRR | 28 |
| EGF RECEPTOR (Thr669) (SEQ ID NO: 3) | RRELVEPLTPSGEA | 13 |
| TH (rat) | | |
| Ser8 (SEQ ID NO:4) | PTPSAPSPQPK | <1 |
| Ser19 | RRAVSEQDAK | <1 |

TABLE 2-continued

Phosphorylation of substrates by ERK1

| SUBSTRATE SOURCE | SEQUENCE | RELATIVE $^{32}$P INCORPORATION (% OF MBP) |
|---|---|---|
| (SEQ ID NO: 5) Ser31 (SEQ ID NO: 7) | KQAEAVTSPR | 5 |
| Ser40 (SEQ ID NO: 6) | GRRQSLIEDAR | <1 |

Table 3 indicates the relative phosphorylation of TH-Ser31-containing peptides by purified ERK2. In Table 3, each value represents the median of three independent determinations, performed in duplicate. 100 percent $^{32}$P incorporation reflects 3.3 μmol/min/mg under the conditions of these assays, as described above.

While variation of the rat TH-Ser31 peptide sequence (SEQ ID NO: 7) resulted in a substrate (SEQ ID NO: 8) that improved ERK-catalyzed $^{32}$P incorporation (Table 2, top), $^{32}$P incorporation into cognate (SEQ ID NO: 9) and type 1 human TH-Ser31 peptides was higher (Table 3, middle). Inclusion of the endogenous FIGRR sequence downstream of the phosphorylation site in TH-Ser31 type 1 human, as well as extending the upstream sequence (SEQ ID NO: 13 and SEQ ID NO: 14), improved the phosphorylation of the Ser31-containing peptides. Subsequent experiments demonstrated that the isoleucine could be omitted without effect upon phosphorylation rate (data not shown). By contrast, peptides derived from the type 2 human TH splice variant (which results in the addition of the residues VRGQ immediately upstream of Ser31) were relatively poor substrates for ERK2 (Table 3, bottom).

TABLE 3

Phosphorylation of TH Ser31-containing peptides by ERK2

| TH-Ser31 SEQUENCE | RELATIVE $^{32}$P INCORPORATION (% 3.3 μmol/min/mg) |
|---|---|
| RAT: | |
| KQAEAVTSPR (SEQ ID NO: 7) | 7 |
| AVTSPRFIGRR (SEQ ID NO: 8) | 9 |
| EAVTSPRFIGRR (SEQ ID NO: 9) | 20 |
| type 1 HUMAN: | |
| EAIMSPRFK (SEQ ID NO: 10) | 21 |
| AIMSPRFIGRR (SEQ ID NO: 11) | 29 |
| EAIMSPRFIGRR (SEQ ID NO: 12) | 41 |
| YQAEAIMSPRFIGRRQ (SEQ ID NO: 13) | 80 |
| YQAEAIMSPRFIGRR-NH2 (SEQ ID NO: 14) | 100 |
| type 2 HUMAN | |
| IMVRGQSPR (SEQ ID NO: 20) | 1 |
| YIMVRGQSPR (SEQ ID NO: 21) | 1 |
| EAIMVRGQSPRFK (SEQ ID NO: 22) | 2 |

Additional peptide substrates were synthesized modeled after the Ser31 of human tyrosine hydroxylase. These new substrates were assayed for the relative phosphorylation by purified ERK2 similar to the experiments that generated Table 3. The results are shown in Table 4. The values represent the mean and standard error of the mean (SEM) of four determinations, performed in duplicate. 100 percent $^{32}$P incorporation reflects 3.0 μmol/min/mg under the conditions of these assays.

TABLE 4

Phosphorylation of TH Ser31-containing peptides by ERK2

| TH-Ser31 SEQUENCE | RELATIVE $^{32}$P INCORPORATION (% 3.0 μmol/min/mg) | |
|---|---|---|
| type 1 HUMAN: | Mean | SEM |
| YQAEAIMSPRFIGRRQ (SEQ ID NO: 13) | 100 | |
| YQAEAIMSPRFIGRR-NH2 (SEQ ID NO: 14) | 117 | 1 |
| QAEAIMSPRFGRR-NH2 (SEQ ID NO: 15) | 107 | 1 |
| YQATGPLSPGPFRR-NH2 (SEQ ID NO: 16) | 164 | 1 |
| QATGPLSPGPFRR-NH2 (SEQ ID NO: 17) | 143 | 1 |
| YQATGPLSPGFRR-NH2 (SEQ ID NO: 18) | 215 | 5 |
| QATGPLSPGFRR-NH2 (SEQ ID NO: 19) | 182 | 2 |

The results in Tables 2, 3, and 4 indicate that the new Ser31 peptides were better substrates for both ERK1 and ERK2 phosphorylation than any other peptide that was tested.

Steady-state kinetic analyses of several of the peptide substrates were determined and the results presented in Table 5. In Table 5, each value represents the median of three independent determinations, performed in duplicate. The apparent $V_{max}$ of ERKtide (SEQ ID NO: 23) was 9.4 μmol/min/mg. Unlike MBP (SEQ ID NO: 1), which has a $K_m$ in, the range of 10–50 μM, all of the peptides tested had a $K_{m(app)}$ that ranged from 0.6 to 2.0 mM. A $K_m$ for MBPtide (SEQ ID NO: 2) was reported to be 1.6 mM, which was decreased to 74 μM by conjugating multiple MBPtide molecules to poly(Lys)$_{87}$. See I. Kameshita et al., 1997. Notably, the original rat TH-Ser31 peptide (SEQ ID NO: 7) exhibited the lowest catalytic efficiency (V/K), whereas substantially higher efficiencies were obtained with type 1 human TH-Ser31 peptides (SEQ ID NO: 10 and SEQ ID NO: 13) and ERKtide (SEQ ID NO: 23), which contain the FGRR sequence downstream of the phosphorylation site. The present $K_{m(app)}$ of ERKtide (SEQ ID NO: 23) (0.6 mM) is comparable to 0.45 mM as described previously by M. J. Robinson et al, "Mutation of position 52 in ERK2 creates a nonproductive binding mode for adenosine 5'-triphosphate," Biochem., vol. 355, pp. 5641–5646 (1996); see also C. N. Prowse et al., "Catalytic reaction pathway for the mitogen-activated protein kinase ERK2," Biochem., vol. 39, pp. 6258–6266 (2000).

TABLE 5

Kinetic constants of peptide substrates for ERK2

| SUBSTRATE | $K_{min(app)}$ mM | $V_{max(app)}$ Relative | V/K |
|---|---|---|---|
| MBPtide: | | | |
| APRTPGGRR (SEQ ID NO: 2) rat TH-Ser31: | 2.0 | 46 | 23 |
| KQAEAVTSPR (SEQ ID NO: 7) human TH type 1: | 1.8 | 9 | 5 |
| EAIMSPRFK (SEQ ID NO: 10) | 1.4 | 42 | 28 |
| YQAEAIMSPRFIGRRQ (SEQ ID NO: 13) ERKtide: | 1.0 | 80 | 80 |
| ATGPLSPFGRR (SEQ ID NO: 23) | 0.6 | 82 | 136 |

It is believed based on sequence similarity that the other Ser31 peptides of human type 1 tyrosine hydroxylase (SEQ ID NO: 14; SEQ ID NO: 15; SEQ ID NO: 16; SEQ ID NO: 17; SEQ ID NO: 18; and SEQ ID NO: 19) will have a similar high catalytic efficiency as seen with SEQ ID NO: 13.

EXAMPLE 3

Comparison of in vitro Assays of ERK Activation in situ

Figure 2:
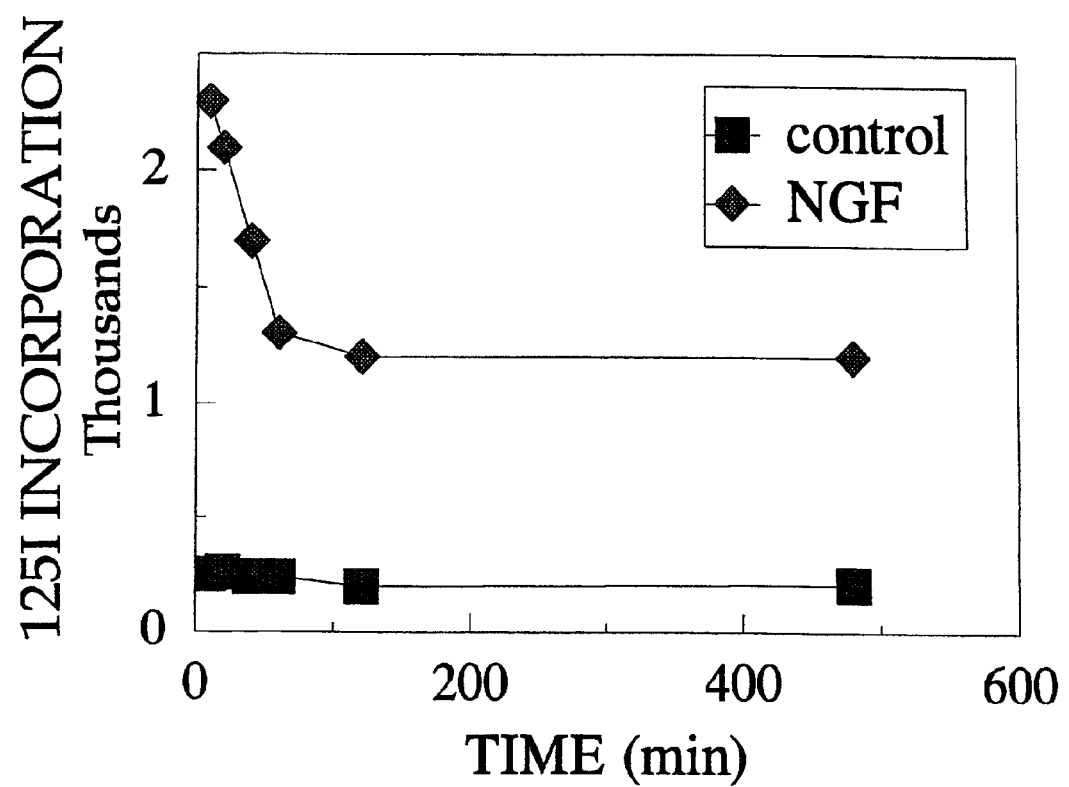
FIG. 2 illustrates the pattern of ERK1/2 activation in PC12 cells treated with and without nerve growth factor using an in vitro blot immunolabeling assay with the diphosphorylated form of ERK1 (ppERK1).
Figure 3:
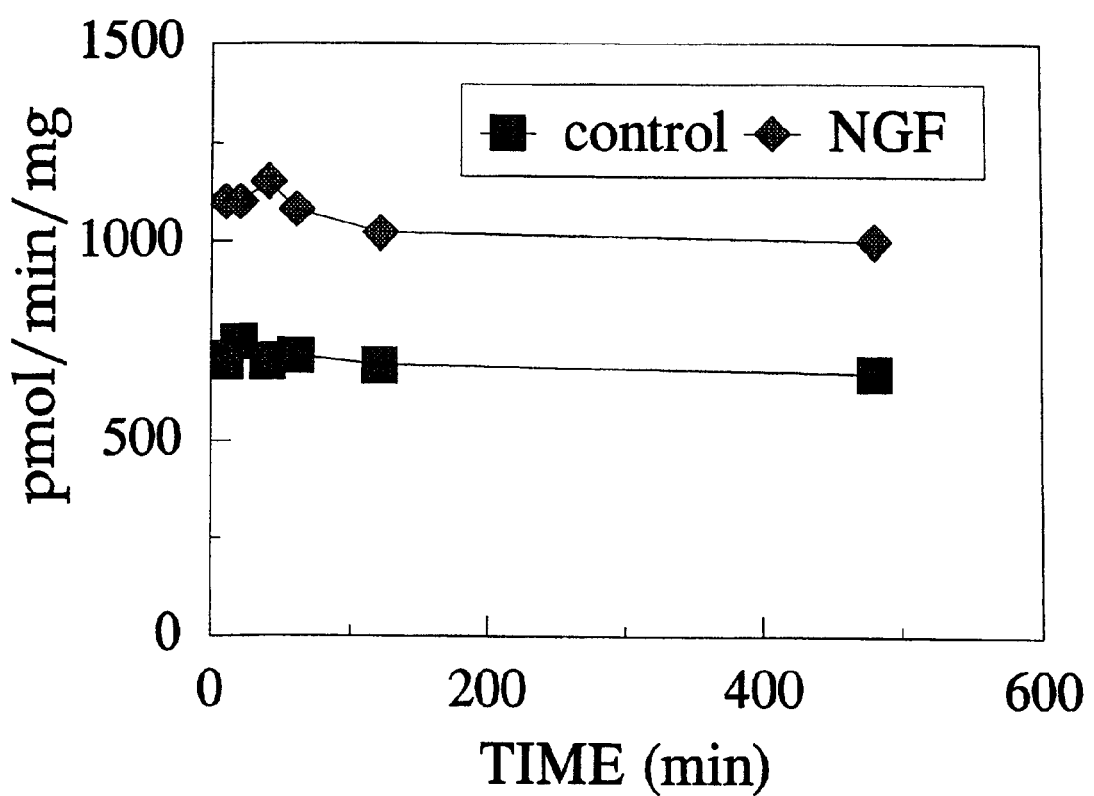
FIG. 3 illustrates the pattern of ERK1/2 activation in PC12 cells treated with and without nerve growth factor using an in vitro kinase assay on cellular extracts with no further purification and using as substrate myelin basic protein (MAP; SEQ ID NO: 1).
Figure 4:
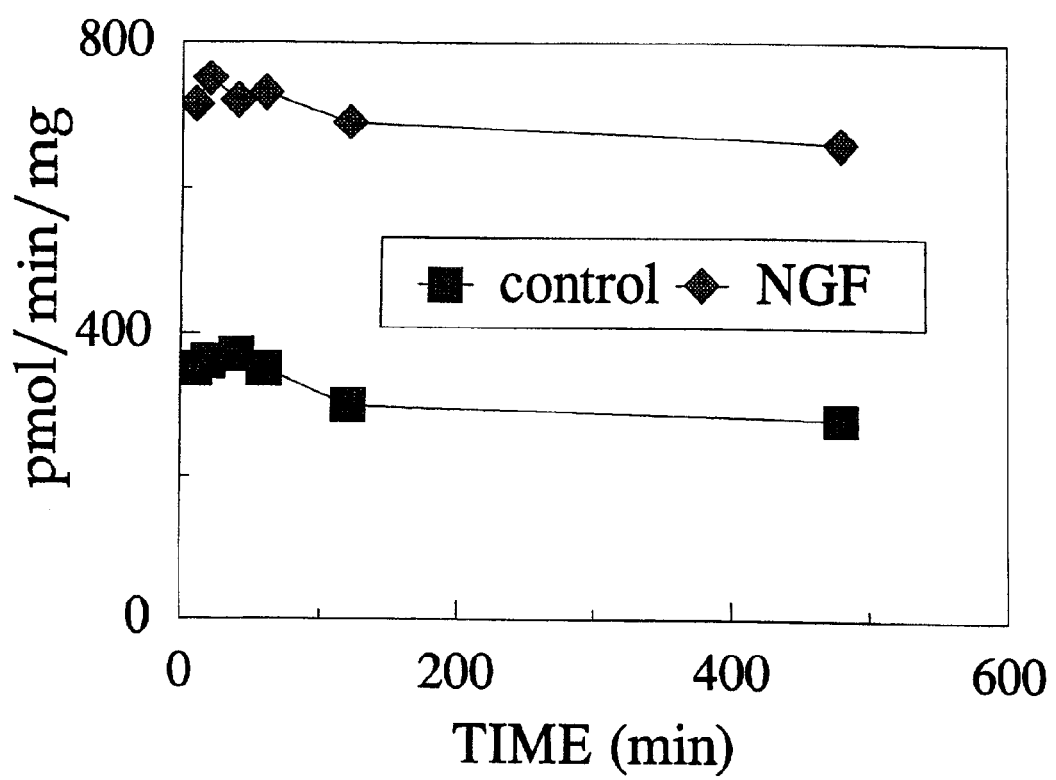
FIG. 4 illustrates the pattern of ERK1/2 activation in PC12 cells treated with and without nerve growth factor using an in vitro kinase assay on cellular extracts with no further purification and using as substrate a peptide of myelin basic protein (MBPtide, APRTGGRR, SEQ ID NO: 2).

Experiments were conducted to test the ability of different substrates to assay for activation of ERK1/2 in situ. PC12 cells were incubated with and without nerve growth factor for about 8 h (480 min), as described in Example 1. Cells were harvested and assayed for ERK1/2 activity by various methods. FIGS. 1 and 2 illustrate results using either a kinase assay performed after removal of other kinases by immunoprecipitation (FIG. 1) or a blot immunolabeling assay (FIG. 2). Both assays produced a qualitatively similar pattern of ERK activation in PC12 cells during prolonged treatment with nerve growth factor (NGF).

However, when a simpler assay using cellular extracts without further kinase purification was used, as shown in the lower panels of FIGS. 3–6, the results varied qualitatively depending upon the substrate used to measure ERK1/2 activity. Higher levels of protein kinase activity were obtained using either MBP (SEQ ID NO: 1) (FIG. 3) or MBPtide (SEQ ID NO: 2) (FIG. 4), despite the presence of EGTA, calmidazolium, and cAMP-dependent protein kinase inhibitor in the assay mix. However, both the pattern and the degree of ERK activation over time using as substrate either MBP (SEQ ID NO: 1) (FIG. 3) or MBPtide (SEQ ID NO: 2) differed from that measured by either the ERK immunoprecipitation or blot immunolabeling assays. (Compare FIGS. 1 and 2 with FIGS. 3 and 4). It is believed that the results in FIGS. 3 and 4 indicate that the assay measured phosphorylation by other protein kinases in addition to that by ERK1 and ERK2.

Figure 5:
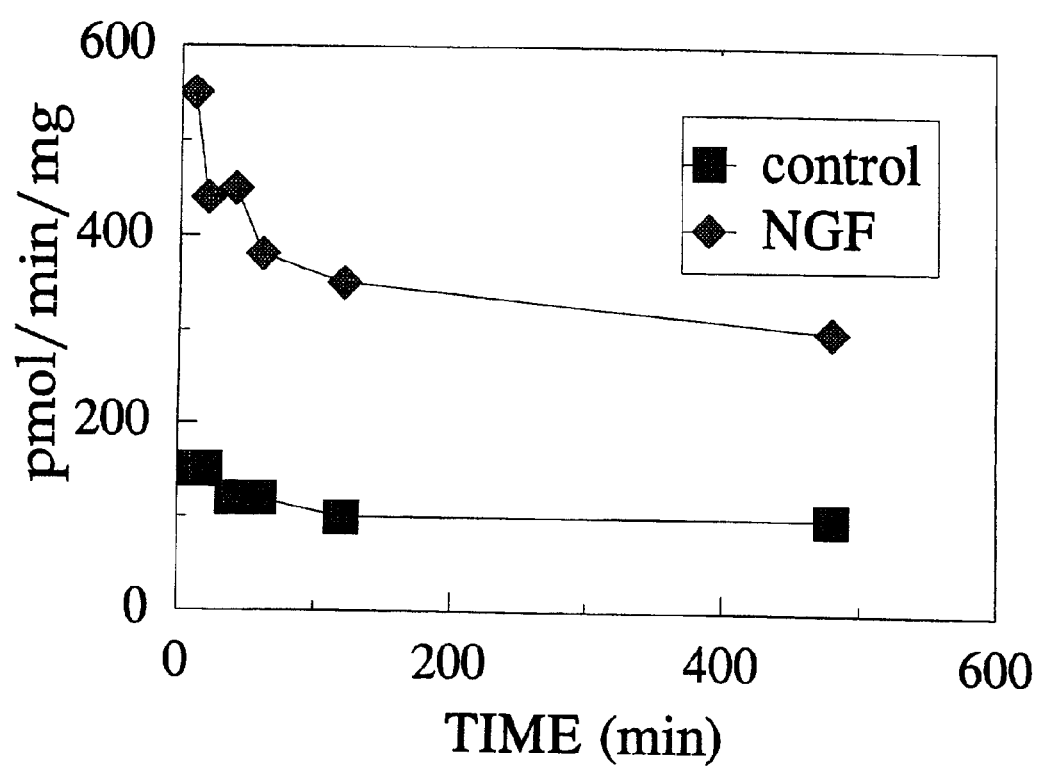
FIG. 5 illustrates the pattern of ERK1/2 activation in PC12 cells treated with and without nerve growth factor using an in vitro kinase assay on cellular extracts with no further purification and using as substrate a peptide modeled after Ser31 in tyrosine hydroxylase in humans (YQAEAIMSPRFIGRRQ, SEQ ID NO: 13).
Figure 6:
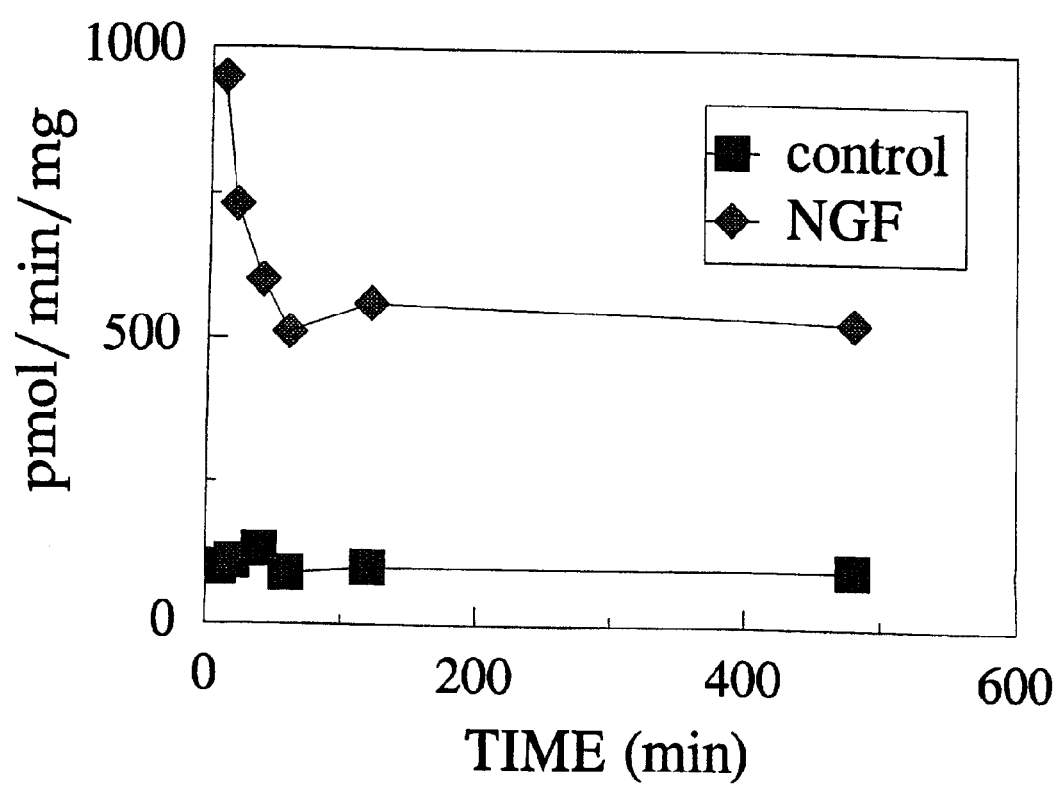
FIG. 6 illustrates the pattern of ERK1/2 activation in PC12 cells treated with and without nerve growth factor using an in vitro kinase assay on cellular extracts with no further purification and using as substrate a known peptide ERKtide (ATGPLSPGPFGRR, SEQ ID NO: 23).

In contrast, both the pattern and degree of ERK activation in the immunoprecipitation and blot immunolabeling assay was faithfully reproduced using as substrate either a type 1 human TH-Ser31 peptide (SEQ ID NO: 13) (FIG. 5) or ERKtide (SEQ ID NO: 23) (FIG. 6). Similar results were seen in phorbol ester-treated PC12 cells (data not shown) and K562 cells (N. G. Ahn, personal communication), indicating that the data presented in FIGS. 5 and 6 are not restricted to either PC12 cells or nerve growth factor treatment.

The validity of assays of ERK activity in cellular extracts depends upon the substrate used. The present data indicate that prior immunoprecipitation is required if either MBP (SEQ ID NO: 1) or MBPtide (SEQ ID NO: 2) is chosen as a substrate. Alternative assays, such as in-gel kinase assays precast with MBP, are expensive. While the separation of ERK1 and ERK2 by molecular mass can isolate their individual activities, issues of renaturation and equilibration of reaction solutions make such assays more cumbersome and less desirable than blot immunolabeling with anti-diphosphoERK antibodies.

The present data demonstrate that in situ ERK activation can be accurately assessed in cellular extracts by using either type 1 human TH-Ser31 peptide (SEQ ID NO: 13) or ERKtide (SEQ ID NO: 23) as the exogenous substrate in a relatively high throughput system. It is believed that similar results will be obtained using the other peptide substrates based on type 1 human TH-Ser31, e.g., SEQ ID NO: 14; SEQ ID NO: 15; SEQ ID NO: 16; SEQ ID NO: 17; SEQ ID NO: 18; and SEQ ID NO: 19.

The new peptide substrates modeled after human tyrosine hydroxylase Ser31 were found to be effective substrates to assay for ERK1/2 activity. The use of these new Ser31 peptides will decrease the amount of peptide required to assay for ERK1/2 activity. In addition, the higher catalytic efficiencies associated with greater specificity for ERK1/2 will enable researchers to assay for activity of ERK1/2 in cellular extracts without prior immunoprecipitation. Such simple assays using cellular extracts can be useful in detecting abnormal ERK1/2 activation patterns, and may help with diagnosis of certain diseases known to show abnormal activation patterns, e.g., Parkinson's and Alzheimer's. See S. M. Kulich et al., 2001.

The complete disclosures of all references cited in this specification are hereby incorporated by reference. Also, incorporated by reference is the following manuscript: J. W. Haycock, "Peptide substrates for ERK1/2: structure-function studies of serine 31 in tyrosine hydroxylase," Journal of Neuroscience Methods, to be published. In the event of an otherwise irreconcilable conflict, however, the present specification shall control.

I claim:

1. A peptide selected from the group consisting of YQAEAIMSPRFIGRRQ (SEQ ID NO: 13), YQAEAIMSPRFIGRR (SEQ ID NO: 14), QAEAIMSPRFGRR (SEQ ID NO: 15), YQATGPLSPGPFRR (SEQ ID NO: 16), QATGPLSPGPFRR (SEQ ID NO: 17), YQATGPLSPGFRR (SEQ ID NO: 18), and QATGPLSPGFRR (SEQ ID NO: 19).

2. A peptide as in claim 1, wherein said peptide is YQAEAIMSPRFIGRRQ (SEQ ID NO: 13).

3. A peptide as in claim 1, wherein said peptide is YQAEAIMSPRFIGRR (SEQ ID NO: 14).

4. A peptide as in claim 1, wherein said peptide is QAEAIMSPRFGRR (SEQ ID NO: 15).

5. A peptide as in claim 1, wherein said peptide is YQATGPLSPGPFRR (SEQ ID NO: 16).

6. A peptide as in claim 1, wherein said peptide is QATGPLSPGPFRR (SEQ ID NO: 17).

7. A peptide as in claim 1, wherein said peptide is YQATGPLSPGFRR (SEQ ID NO: 18).

8. A peptide as in claim 1, wherein said peptide is QATGPLSPGFRR (SEQ ID NO: 19).

9. A method to assay a sample for the presence of activated extracellular signal-regulated protein kinase 1 or 2, said method comprising the steps of:
   (a) forming a mixture comprising the sample, ATP, and a peptide selected from the group consisting of YQAEAIMSPRFIGRRQ (SEQ ID NO: 13), YQAEAIMSPRFIGRR (SEQ ID NO: 14), QAEAIMSPRFGRR (SEQ ID NO: 15), YQATGPLSPGPFRR (SEQ ID NO: 16), QATGPLSPGPFRR (SEQ ID NO: 17), YQATGPLSPGFRR (SEQ ID NO: 18), and QATGPLSPGFRR (SEQ ID NO: 19);
   (b) incubating the mixture under conditions conducive to phosphorylation of the peptide if activated extracellular signal-regulated protein kinase 1 or 2 is present; and
   (c) measuring the degree of phosphorylation of the peptide; whereby the presence and degree of such phosphorylation is measure of any activated extracellular signal-regulated protein kinase 1 or 2 in the sample.

10. The method according to claim 9, wherein the ATP is radiolabeled, and wherein said measuring step comprises measuring the radioactivity of the phosphorylated peptide.

11. The method according to claim 9, wherein the peptide is YQAEAIMSPRFIGRRQ (SEQ ID NO: 13).

12. The method according to claim 9, wherein the peptide is YQAEAIMSPRFIGRR (SEQ ID NO: 14).

13. The method according to claim 9, wherein the peptide is QAEAIMSPRFGRR (SEQ ID NO: 15).

14. The method according to claim 9, wherein the peptide is YQATGPLSPGPFRR (SEQ ID NO: 16).

15. The method according to claim 9, wherein the peptide is QATGPLSPGPFRR (SEQ ID NO: 17).

16. The method according to claim 9, wherein the peptide is YQATGPLSPGFRR (SEQ ID NO: 18).

17. The method according to claim 9, wherein the peptide is QATGPLSPGFRR (SEQ ID NO: 19).

18. A kit for assaying for the presence of activated extracellular signal-regulated protein kinase 1 or 2 in a sample, said kit comprising the following packaged compositions:
   (a) labeled ATP in a first container; and
   (c) a peptide in a second container, said peptide selected from the group consisting of YQAEAIMSPRFIGRRQ (SEQ ID NO: 13), YQAEAIMSPRFIGRR (SEQ ID NO: 14), QAEAIMSPRFGRR (SEQ ID NO: 15), YQATGPLSPGPFRR (SEQ ID NO: 16), QATGPLSPGPFRR (SEQ ID NO: 17), YQATGPLSPGFRR (SEQ ID NO: 18), and QATGPLSPGFRR (SEQ ID NO: 19).

19. A kit according to claim 18, wherein said ATP is radiolabeled.

20. A kit according to claim 18, wherein said peptide is YQAEAIMSPRFIGRRQ (SEQ ID NO: 13).

21. A kit according to claim 18, wherein said peptide is YQAEAIMSPRFIGRR (SEQ ID NO: 14).

22. A kit according to claim 18, wherein said peptide is QAEAIMSPRFGRR (SEQ ID NO: 15).

23. A kit according to claim 18, wherein said peptide is YQATGPLSPGPFRR (SEQ ID NO: 16).

24. A kit according to claim 18, wherein said peptide is QATGPLSPGPFRR (SEQ ID NO: 17).

25. A kit according to claim 18, wherein said peptide is YQATGPLSPGFRR (SEQ ID NO: 18).

26. A kit according to claim 18, wherein said peptide is QATGPLSPGFRR (SEQ ID NO: 19).

* * * * *

SEQUENCE LISTING

<160> NUMBER OF SEQ ID NOS: 24

<210> SEQ ID NO 1
<211> LENGTH: 169

```
<212> TYPE: PRT
<213> ORGANISM: Bos taurus

<400> SEQUENCE: 1

Ala Ala Gln Lys Arg Pro Ser Gln Arg Ser Lys Tyr Leu Ala Ser Ala
1               5                   10                  15

Ser Thr Met Asp His Ala Arg His Gly Phe Leu Pro Arg His Arg Asp
            20                  25                  30

Thr Gly Ile Leu Asp Ser Leu Gly Arg Phe Phe Gly Ser Asp Arg Gly
            35                  40                  45

Ala Pro Lys Arg Gly Ser Gly Lys Asp Gly His His Ala Ala Arg Thr
    50                  55                  60

Thr His Tyr Gly Ser Leu Pro Gln Lys Ala Gln Gly His Arg Pro Gln
65                  70                  75                  80

Asp Glu Asn Pro Val Val His Phe Phe Lys Asn Ile Val Thr Pro Arg
                85                  90                  95

Thr Pro Pro Pro Ser Gln Gly Lys Gly Arg Gly Leu Ser Leu Ser Arg
                100                 105                 110

Phe Ser Trp Gly Ala Glu Gly Gln Lys Pro Gly Phe Gly Tyr Gly Gly
            115                 120                 125

Arg Ala Ser Asp Tyr Lys Ser Ala His Lys Gly Leu Lys Gly His Asp
    130                 135                 140

Ala Gln Gly Thr Leu Ser Lys Ile Phe Lys Leu Gly Gly Arg Asp Ser
145                 150                 155                 160

Arg Ser Gly Ser Pro Met Ala Arg Arg
                165

<210> SEQ ID NO 2
<211> LENGTH: 8
<212> TYPE: PRT
<213> ORGANISM: Artificial Sequence
<220> FEATURE:
<223> OTHER INFORMATION: This sequence is MBPtide (Thr 97).

<400> SEQUENCE: 2

Ala Pro Arg Thr Pro Gly Gly Arg
1               5

<210> SEQ ID NO 3
<211> LENGTH: 14
<212> TYPE: PRT
<213> ORGANISM: Artificial Sequence
<220> FEATURE:
<223> OTHER INFORMATION: This sequence is EGF Receptor (Thr669).

<400> SEQUENCE: 3

Arg Arg Glu Leu Val Glu Pro Leu Thr Pro Ser Gly Glu Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: This sequence is TH (rat) Ser8.

<400> SEQUENCE: 4

Pro Thr Pro Ser Ala Pro Ser Pro Gln Pro Lys
1               5                   10

<210> SEQ ID NO 5
```

```
<211> LENGTH: 10
<212> TYPE: PRT
<213> ORGANISM: Artificial Sequence
<220> FEATURE:
<223> OTHER INFORMATION: This sequence is TH (rat) Ser19.

<400> SEQUENCE: 5

Arg Arg Ala Val Ser Glu Gln Asp Ala Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: This sequence is TH (rat) Ser40.

<400> SEQUENCE: 6

Gly Arg Arg Gln Ser Leu Ile Glu Asp Ala Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: This sequence is based on TH-Ser31 (rat).

<400> SEQUENCE: 7

Lys Gln Ala Glu Ala Val Thr Ser Pro Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: This sequence is based on TH-Ser31 (rat).

<400> SEQUENCE: 8

Ala Val Thr Ser Pro Arg Phe Ile Gly Arg Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: This sequence is based on TH-Ser31 (rat).

<400> SEQUENCE: 9

Glu Ala Val Thr Ser Pro Arg Phe Ile Gly Arg Arg
1               5                   10

<210> SEQ ID NO 10
<211> LENGTH: 9
<212> TYPE: PRT
<213> ORGANISM: Artificial Sequence
<220> FEATURE:
<223> OTHER INFORMATION: This sequence is based on TH-31: type 1 HUMAN.

<400> SEQUENCE: 10

Glu Ala Ile Met Ser Pro Arg Phe Lys
1               5

<210> SEQ ID NO 11
<211> LENGTH: 11
```

```
<212> TYPE: PRT
<213> ORGANISM: Artificial Sequence
<220> FEATURE:
<223> OTHER INFORMATION: This sequence is based on TH-31: type 1 HUMAN.

<400> SEQUENCE: 11

Ala Ile Met Ser Pro Arg Phe Ile Gly Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: This sequence is based on TH-31: type 1 HUMAN.

<400> SEQUENCE: 12

Glu Ala Ile Met Ser Pro Arg Phe Ile Gly Arg Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: This sequence is new and based on TH-31: type 1
      HUMAN.

<400> SEQUENCE: 13

Tyr Gln Ala Glu Ala Ile Met Ser Pro Arg Phe Ile Gly Arg Arg Gln
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: This sequence is new and based on TH-31: type 1
      HUMAN.

<400> SEQUENCE: 14

Tyr Gln Ala Glu Ala Ile Met Ser Pro Arg Phe Ile Gly Arg Arg
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: This sequence is new and based on TH-31: type 1
      HUMAN.

<400> SEQUENCE: 15

Gln Ala Glu Ala Ile Met Ser Pro Arg Phe Gly Arg Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: This sequence is new and based on TH-31:  type
      1 HUMAN.

<400> SEQUENCE: 16

Tyr Gln Ala Thr Gly Pro Leu Ser Pro Gly Pro Phe Arg Arg
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: This application is new and based on TH-31:
      type 1 HUMAN.

<400> SEQUENCE: 17

Gln Ala Thr Gly Pro Leu Ser Pro Gly Pro Phe Arg Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: This sequence is new and based on TH-31: type 1
      HUMAN.

<400> SEQUENCE: 18

Tyr Gln Ala Thr Gly Pro Leu Ser Pro Gly Phe Arg Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: This sequence is new and based on TH-31: type 1
      HUMAN.

<400> SEQUENCE: 19

Gln Ala Thr Gly Pro Leu Ser Pro Gly Phe Arg Arg
1               5                   10

<210> SEQ ID NO 20
<211> LENGTH: 9
<212> TYPE: PRT
<213> ORGANISM: Artificial Sequence
<220> FEATURE:
<223> OTHER INFORMATION: This sequence is based on TH-Ser31: type 2
      HUMAN.

<400> SEQUENCE: 20

Ile Met Val Arg Gly Gln Ser Pro Arg
1               5

<210> SEQ ID NO 21
<211> LENGTH: 10
<212> TYPE: PRT
<213> ORGANISM: Artificial Sequence
<220> FEATURE:
<223> OTHER INFORMATION: This sequence is based on TH-Ser31: type 2
      HUMAN.

<400> SEQUENCE: 21

Tyr Ile Met Val Arg Gly Gln Ser Pro Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: This sequence is based on TH-Ser31: type 2
      HUMAN.

```
<400> SEQUENCE: 22

Glu Ala Ile Met Val Arg Gly Gln Ser Pro Arg Phe Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: This sequence is ERKtide.

<400> SEQUENCE: 23

Ala Thr Gly Pro Leu Ser Pro Phe Gly Arg Arg
1               5                   10

<210> SEQ ID NO 24
<211> LENGTH: 20
<212> TYPE: PRT
<213> ORGANISM: Artificial Sequence
<220> FEATURE:
<223> OTHER INFORMATION: This sequence is a peptide inhibitor of cyclic
      AMP-dependent protein kinase.

<400> SEQUENCE: 24

Thr Thr Tyr Ala Asp Phe Ile Ala Ser Gly Arg Thr Gly Arg Arg Asn
1               5                   10                  15

Ala Leu His Asp
            20
```